United States Patent
Vincent et al.

[11] Patent Number: 5,993,410
[45] Date of Patent: Nov. 30, 1999

[54] ADJUSTABLE PROBE

[75] Inventors: Douglas E. Vincent, Goleta, Calif.;
John Johnston, Washington, N.J.;
Richard Upcavage, Farless Hills, Pa.

[73] Assignee: Cabot Technology Corporation, Wilmington, Del.

[21] Appl. No.: 08/889,654

[22] Filed: Jul. 8, 1997

[51] Int. Cl.⁶ .................................................. A61M 1/00
[52] U.S. Cl. ................................ 604/27; 604/33; 604/322
[58] Field of Search ........................... 604/27, 33, 32, 604/35, 118, 169, 240, 248, 249, 326, 905, 39, 45, 43, 284; 128/912; 137/331, 333, 908, 625.38, 616.5; 251/904, 87, 88, 211, 322, 325; 285/121.5, 145.2, 144.1, 147.1, 147.3, 148.1, 148.7

[56] References Cited

U.S. PATENT DOCUMENTS

| | | | |
|---|---|---|---|
| 3,900,221 | 8/1975 | Fouts | 285/276 |
| 4,497,468 | 2/1985 | Hubbard et al. | 251/117 |
| 4,696,669 | 9/1987 | Menhusen . | |
| 4,708,717 | 11/1987 | Deane et al. . | |
| 5,056,575 | 10/1991 | Glossop | 137/883 |
| 5,063,968 | 11/1991 | Bartholomew | 138/109 |
| 5,188,591 | 2/1993 | Dorsey, III . | |
| 5,242,387 | 9/1993 | Loughlin | 604/43 |
| 5,244,459 | 9/1993 | Hill | 604/33 |
| 5,254,083 | 10/1993 | Gentelia et al. . | |
| 5,257,825 | 11/1993 | Wilcock . | |
| 5,328,478 | 7/1994 | McVay . | |
| 5,391,145 | 2/1995 | Dorsey, III . | |
| 5,449,145 | 9/1995 | Wortrich . | |
| 5,449,357 | 9/1995 | Zinnanti . | |
| 5,634,897 | 6/1997 | Dance et al. | 604/35 |
| 5,642,726 | 7/1997 | Owens et al. | 128/200.26 |
| 5,782,575 | 7/1998 | Vincent et al. | 403/270 |

*Primary Examiner*—Corrine McDermott
*Assistant Examiner*—Sharon Finkel
*Attorney, Agent, or Firm*—Austin R. Miller

[57] ABSTRACT

A probe is provided for adjustable use in the right or left hand of a user. It includes a valve barrel that can be rotated with respect to the probe's body so that the relative position of a valve port can be adjusted according to the preference of the user.

21 Claims, 5 Drawing Sheets ary. The adjustment
ADJUSTABLE PROBE

BACKGROUND OF THE INVENTION

This invention relates to a probe for use during a surgical procedure. In particular, this invention relates to a probe that is adjustable so that it can be held comfortably in the hands of a surgeon or other user.

FIELD OF THE INVENTION

It is important to provide medical devices that are comfortable and convenient to use by surgeons and others. It is especially desirable to provide devices that are adaptable to the needs and preferences of various users. For example, probes such as those used for suction or irrigation of an operative site are frequently used during laparoscopic procedures. Such probes are preferably suited for right- or left-handed use and for adjustment to accommodate the needs of various users.

Attempts have been made in the past to provide a probe that meets these needs. For example, U.S. Pat. Nos. 5,188,591 and 5,391,145 to James H. Dorsey, III and U.S. Pat. No. 5,449,357 to William J. Zinnanti each describes a suction and irrigation probe which has symmetrically opposed probe ports on either end of a trumpet valve. Such probes were intended to permit right- or left-handed operation by means of reversible assembly of the probe's shaft on one side of the valve or the other prior to use of the probe. Another suction and irrigation probe is described in U.S. Pat. No. 5,449,145 to Theodore S. Wortrich in which radial suction and irrigation ports are fixed along the plane shared by two trumpet valves, or at a slight angle thereto.

Nevertheless, there remains a need for a probe that easily and efficiently accommodates both right- and left-handed use. Also, it would be a significant benefit to provide a probe that can be readily adjusted during a medical procedure without sacrificing the probe's functional performance. Such a feature would accommodate multiple users and users who may wish to alternate hands by passing the probe from one hand to another during a procedure.

OBJECTS OF THE INVENTION

It is an object of this invention to provide a probe that is easily adjustable for right- or left-handed operation.

It is another object of this invention to provide a probe that is adjustable to meet the requirements and preferences of various users.

It is still another object of this invention to provide a probe that can be easily adjusted during a medical procedure.

It is yet another object of this invention to achieve the foregoing objects while providing a sturdy and reliable probe.

SUMMARY OF THE INVENTION

A hand-held surgical device is provided for controlling the flow of liquid or gaseous fluid into or out from a surgical patient. The device is uniquely adapted for use in the right or left hand and is also adapted for alternating use between hands.

The device includes a body that defines a flow passageway through which fluid flows toward or from the patient. At least one piston valve connected to the body of the device includes a barrel as well as a port in the barrel that is positioned for flow into or out from the valve.

The barrel is mounted to the body of the device so that the barrel can rotate about its axis. Such rotation advantageously changes the orientation of the barrel's port. This feature makes it possible to adjust the position of a flexible hose that may be attached to the port so that its position can accommodate the needs of various users or the varying needs of a particular user during a particular procedure. The adjustment of the orientation of the barrel's port can be performed during use of the device in a preferred embodiment.

DETAILED DESCRIPTION OF THE INVENTION

Figure 1:
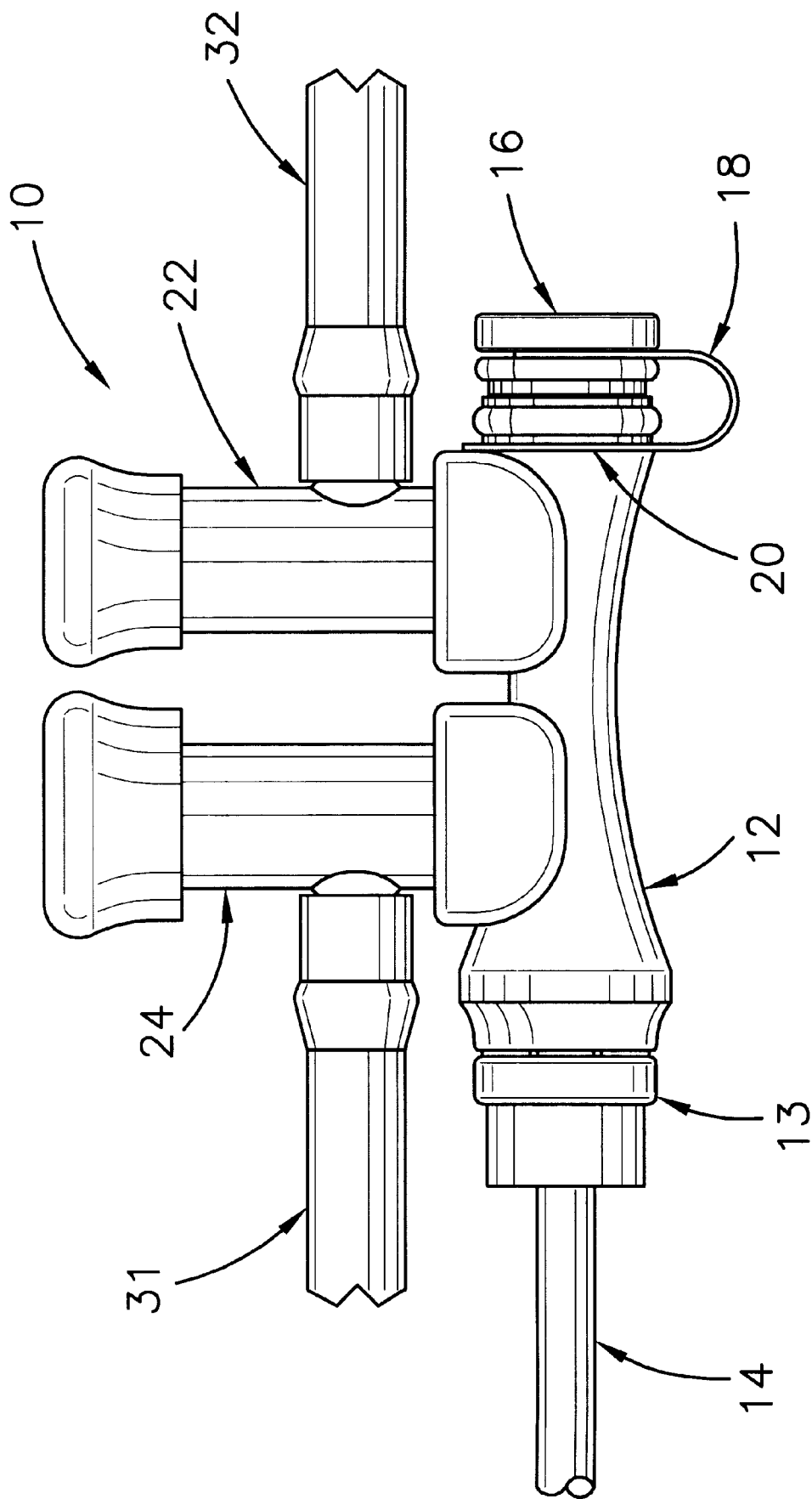
FIG. 1 shows a side view of an embodiment of a suction and irrigation probe according to this invention.

It will be appreciated that this invention is not limited to the specific embodiments selected for illustration in the drawings and described herein. It will also be appreciated that the drawings are merely illustrative and are not necessarily to scale. The invention is defined separately in the appended claims.

FIGS. 1–4 illustrate an embodiment of a probe according to this invention, generally indicated by the numeral "10". Although the embodiment of probe 10 selected for illustration is adapted for suction and irrigation of an operative site by removing and introducing liquid or gaseous fluid from and to the site, respectively, this invention applies equally to probes that are solely used for suction or for irrigation as well as any other types of hand-held probes that could benefit from features of the invention. Also, this invention applies to probes that are intended for disposable use as well as those intended for sterilization and re-use. While probe 10 is described in the context of endoscopic and laparoscopic surgical procedures and related procedures, probe 10 is contemplated for use during any procedure involving delivery or removal of fluid.

Referring to FIG. 1, probe 10 includes a probe body portion 12 that is sized and shaped to be held within the hand of a surgeon during a medical procedure. Probe body 12 is preferably molded from a polymeric or plastic material such as clear or opaque ABS, for example. Probe 10 also includes a tubular probe shaft 14 extending from an end of probe body 12 and connected to body 12 by an adapter or connector 13. Probe shaft 14 is adapted for insertion into a patient and into an operative site in the conventional manner. An end cap 16 is provided at the opposite end of probe body 12 from probe shaft 14. End cap 16 prevents the flow of liquid or gaseous fluid from the probe body 12. End cap 16 is attached by means of a strap 18 that is connected to an attachment ring 20 positioned around the end of probe body 12. End cap 16 is removable and replaceable so that surgical instruments, such as electrocautery probes for example, can be inserted through probe body 12, through probe shaft 14, and into the operative site. Probe body 12 can also include a palm rest (not shown), which may be preferred for user comfort.

Probe 10 also includes an irrigation valve 22 and a suction valve 24, both of which extend upwardly from the top surface of probe body 12 in this embodiment. The irrigation valve 22 is adapted to control the delivery of fluid, such as irrigation liquid for example, into the operative site. Such fluid is delivered to irrigation valve 22 through a flexible hose 32. The suction valve is adapted to control the suction or aspiration or evacuation of liquid or gaseous fluid, such as irrigation fluid, blood, tissue, other solid debris, and smoke for example, from the operative site. Such fluid is removed from suction valve 24 through a flexible hose 31. Such a valve system is frequently referred to as a so-called "trumpet valve". The operation of valves 22 and 24 to control suction and irrigation will be described later.

Figure 2:
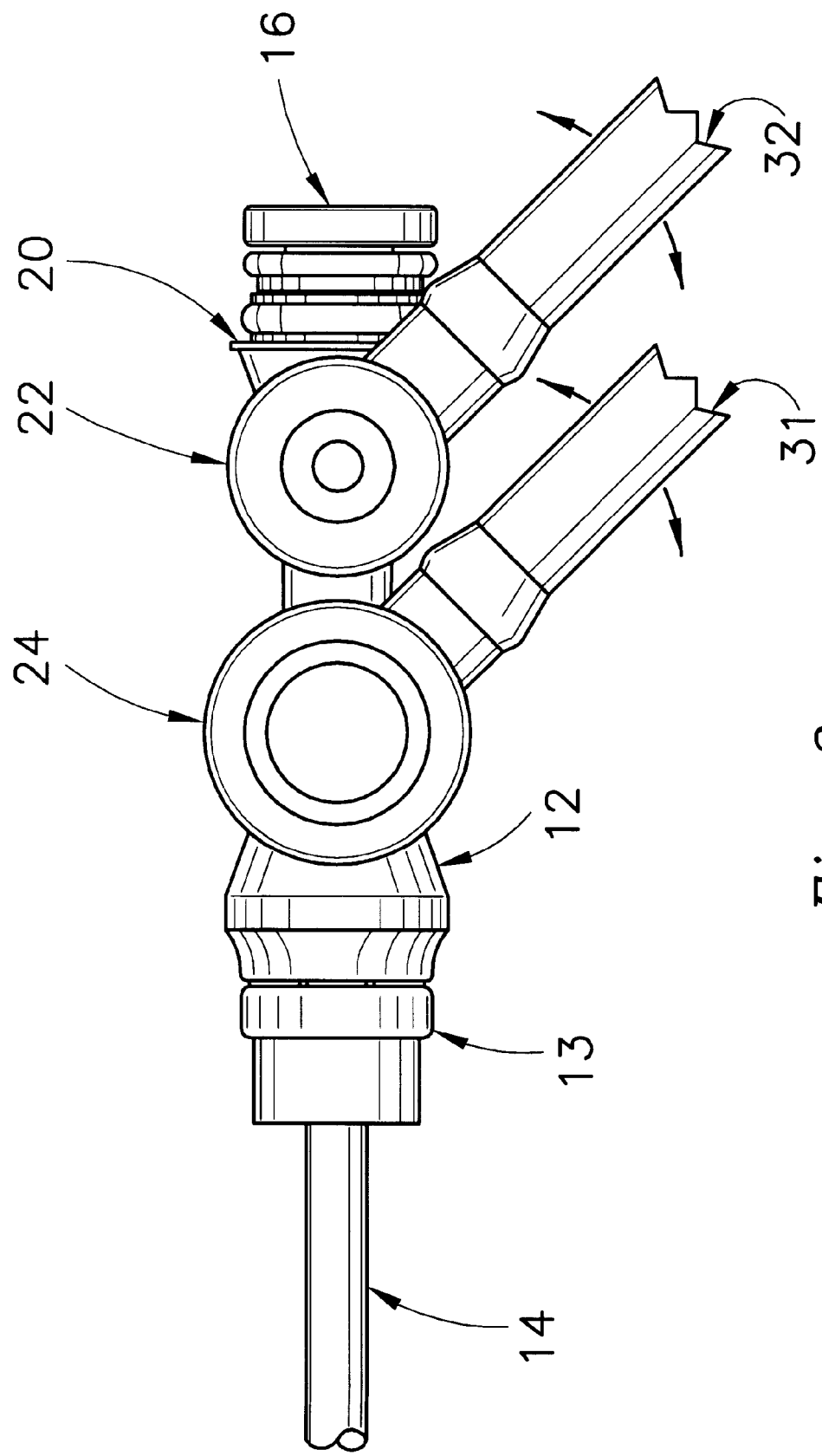
FIG. 2 shows a top view of the suction and irrigation probe shown in FIG. 1.

Referring now to FIG. 2, a top view of probe 10 illustrates one possible embodiment of a feature of this invention. As indicated by the arrows adjacent to hoses 31 and 32, the irrigation valve 22 and suction valve 24 are connected to probe body 12 for rotation about their respective axes so that their barbed fluid connections can be rotated into a variety of positions with respect to the axes of probe body 12 and probe shaft 14. In FIG. 2, both of the barbs are oriented in substantially the same direction but can be rotated in either direction, as needed or desired. This feature permits the user of probe 10 to rotate valves 22 and 24 and their respective fluid hoses 31 and 32 either prior to a medical procedure, during a medical procedure, or even "on the fly" during use of probe 10 for suction or irrigation of an operative site. Such "on the fly" adjustment can preferably be performed while suction or irrigation is underway and while the probe shaft 14 remains in the patient. This preferred feature permits the user or users to adjust probe 10 at any time to be comfortably held in the right hand, the left hand, for alternative movement between the right and left hands, or merely for adjustment of the relative positions of the suction and irrigation hoses so that they do not interfere with surgical activities.

Figure 3:
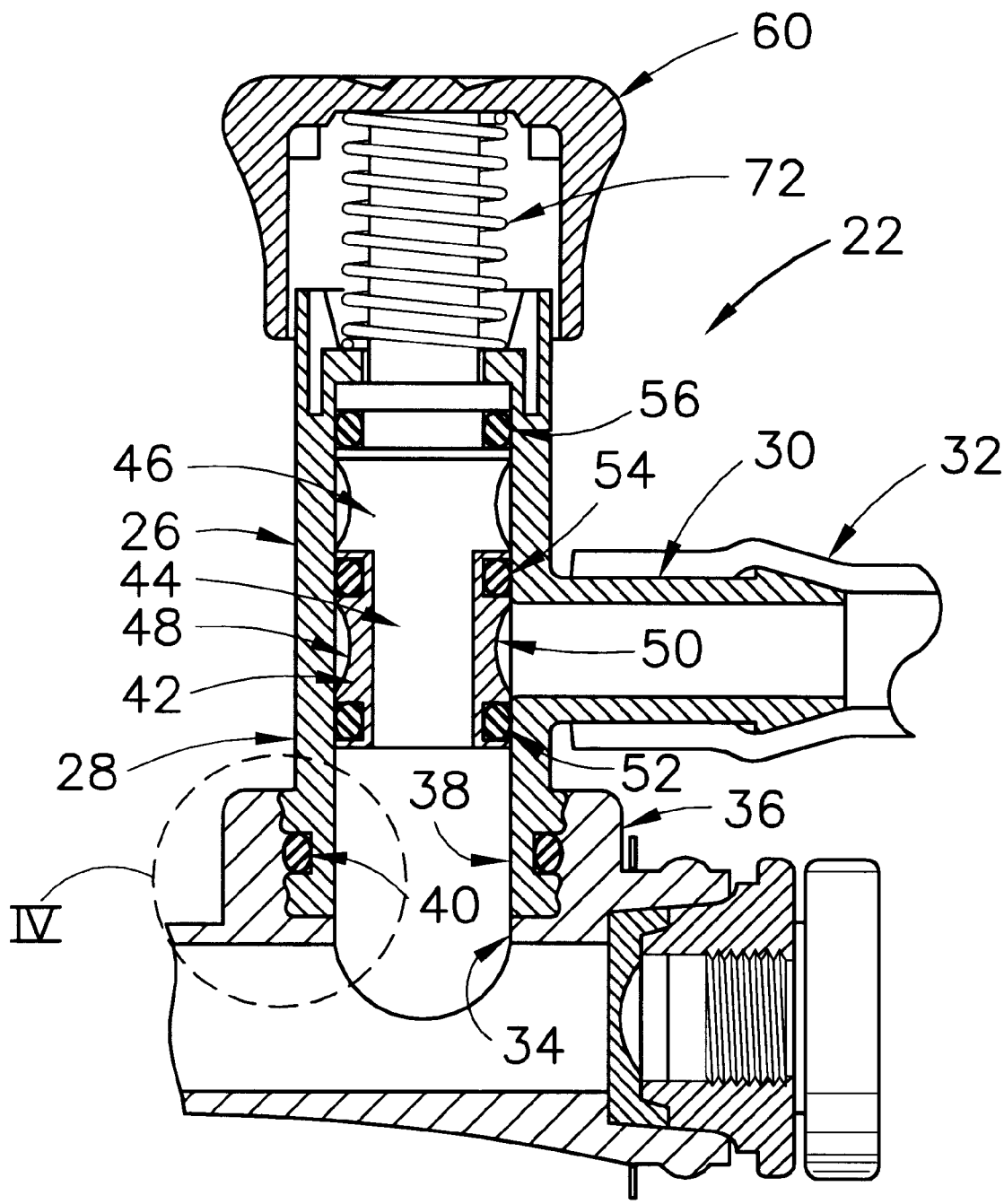
FIG. 3 shows a cross-sectional side view of a portion of the suction and irrigation probe shown in FIG. 1.

Referring now to FIG. 3, a cross-sectional side view of a portion of probe 10 illustrates a preferred structure of irrigation valve 22. Details of suction valve 24 are not shown, but it will be appreciated that the structure of both valves may be the same or substantially the same. In the illustrated embodiment, suction valve 24 is preferably adapted to remove fluid from a surgical site in the form of a liquid or a gas while the irrigation valve 22 is most preferably adapted to control the flow of irrigation liquid into the surgical site. As shown in FIG. 2, the tops of the valves preferably differ in color and/or structure so that a surgeon can quickly differentiate them from one another. Also, suction valve 24 optionally includes a smoke evacuation feature. For example, suction valve 24 is optionally adapted to facilitate partial suction or "sipping" of an operative site. Such "sipping" is preferred for smoke or vapor evacuation which may be necessary when a cauterization procedure conducted in the operative site generates smoke that obstructs the surgeon's view.

As shown in FIG. 3, irrigation valve 22 includes a barbed tube 26 having a substantially cylindrical and hollow valve barrel 28 and a barb 30 that extends radially outwardly from the wall of barrel 28 to form a valve port. Barb 30 of barbed tube 26 is adapted for engaging an end of a flexible hose 32 such as those commonly used for fluid delivery. Flexible hose 32 is connected to an irrigation source (not shown).

Barbed tube 26 is connected to probe body 12 (FIG. 1) adjacent to a body opening 34 formed in probe body 12. Accordingly, when irrigation valve 22 (FIG. 3) is in an open position, a passageway is defined for the flow of liquid or gaseous fluids through flexible hose 32, into barb 30, through barrel 28, and into the operative site through probe body 12 and probe shaft 14, (FIG. 1).

The preferred manner in which barbed tube 26 is mounted to probe body 12 is depicted in FIG. 3 and will later be described in further detail with reference to FIG. 4. Probe body 12 includes a boss 36 which defines a body opening 34. Opening 34 accommodates a mounting portion 38 of barrel 28. This mounting portion 38 of barrel 28 captures an O-ring 40 to create a fluid-tight seal between probe body 12 and barrel 28 to prevent leakage into or out from the probe body between those components.

As will be described further with reference to FIG. 4, mounting portion 38 of barrel 28 is uniquely adapted to permit rotation of barbed tube 26 about the vertical axis of barrel 28 (in this embodiment) without requiring longitudinal movement of barbed tube 26 upward or downward along the axis of barrel 28. Also, this connection between mounting portion 38 and boss 36 is adapted to permit such rotation while maintaining a fluid-tight seal between the components. Further, this connection is adapted to provide a connection that is capable of withstanding high pull-out forces so that barbed tube 26 cannot be easily separated from probe body 12 even during the most rigorous use of probe 10.

Still referring to FIG. 3, irrigation valve 22 also includes a piston 42 that is mounted for reciprocal longitudinal movement within barrel 28 of barbed tube 26 along a piston axis. Piston 42 is provided with a piston bore 44 along the piston's axis to permit the flow of liquid or gaseous fluid therethrough. Piston 42 is also provided with a transverse circular through-hole 46 that is in fluid flow communication with, and substantially perpendicular to, piston bore 44. Provided on an outer surface of piston 42 is a pair of recesses 48 and 50 that are separated from one another by about 180°. Recess 50 is aligned with barb 30 in FIG. 3.

Recesses 48 and 50 are especially desirable for probes where the pistons are mounted on the side of the probe body, such as the alternative embodiment illustrated in FIG. 5, which will be described in detail later. In such an embodiment, recesses 48 and 50 allow an instrument to be passed through the instrument channel in the probe's body without any interference. It will be understood that, if such recesses were not present, the body of the piston could protrude slightly into the instrument channel within the probe body and an instrument could then strike the piston. Accordingly, recesses 48 and 50, while preferable for some embodiments of the probe according to this invention, may not be required for an embodiment wherein the instrument channel is on the bottom portion of the probe body and the barbed tubes are mounted above the instrument channel because the piston in such an embodiment does not protrude into the instrument channel.

Seals are provided between piston 42 and the interior surface of barrel 28 by means of three O-rings. A lower O-ring 52 is provided in a groove positioned adjacent to the bottom edge of piston 42 and below recesses 48 and 50. A middle O-ring 54 is provided in a groove positioned above recesses 48 and 50 and below through-hole 46. An upper O-ring 56 is provided in a groove positioned above through-hole 46.

Piston 42 is provided with a shoulder above O-ring 56 for abutment against a stop formed near the top of barbed tube 26 for the purpose of preventing upward movement of piston 42 beyond the position shown in FIG. 3. In the top of piston 42 is formed a blind hole (not shown), the purpose of which will be made clear later.

Irrigation valve 22 also includes a finger rest 60 adapted for contact by the surgeon's finger during use of probe 10. Finger rest 60 includes a downwardly extending stud (not shown) which is adapted to be engaged within the blind hole (not shown) formed in the top of piston 42, preferably by ultrasonic welding.

Still referring to FIG. 3, a compression spring 72 is provided to bias the finger rest 60 toward its upper-most position as shown, wherein the shoulder of piston 42 contacts the stop at the top of barrel 28. Compression spring 72 is mounted between a lower surface of finger rest 60 and an upper surface of barrel 28 of barbed tube 26 so that finger rest 60 is returned to the position shown in FIG. 3, when released.

Figure 4:
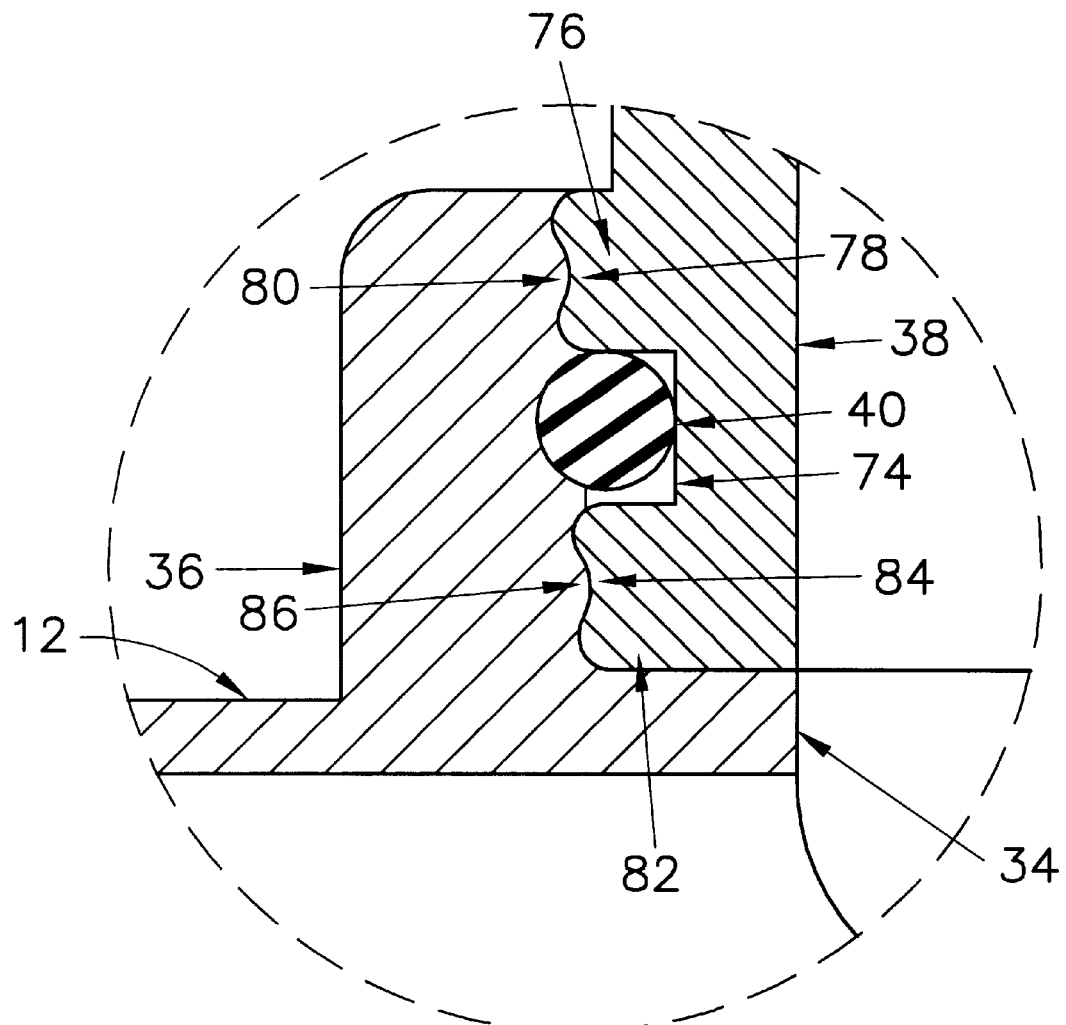
FIG. 4 shows a cross-sectional side view of the detail defined in FIG. 3.

Referring now to FIG. 4, the detail defined in FIG. 3 will now be described to illustrate the preferred embodiment of this invention. Specifically, FIG. 4 illustrates a preferred manner in which mounting portion 38 of barrel 28 is mounted within boss 36 of probe body 12. Mounting portion 38 is provided with an O-ring groove 74 which is sized and shaped to capture O-ring 40. A radial seal between barbed tube 26 and probe body 12 is formed by a seal between O-ring 40 and an interior surface of O-ring groove 74 and between O-ring 40 and an interior surface of boss 36. Positioned above O-ring groove 74 on mounting portion 38 is an upper flange 76 that extends radially outwardly from barrel 28 of barbed tube 26. Upper flange 76 includes on its outermost surface a radial groove 78 that is sized and shaped for snap-in engagement with a radial bead 80 formed on an interior or inner surface of boss 36. Below O-ring groove 74 is a lower flange 82 that also extends radially outwardly from barrel 28 of barbed tube 26. Lower flange 82 also includes a radial groove 84 that is sized and shaped to provide snap-in engagement with a radial bead 86 formed on an interior surface of boss 36.

As illustrated in FIG. 4, the preferred construction of barbed tube 26 and probe body 12 permits a snap-in engagement between those two components. Such a preferred connection confers several significant benefits. First, it permits a secure engagement between the components that cannot be easily disengaged during even the most rigorous use of probe 10 throughout a surgical procedure. For example, the force used to install barbed tube 26 into probe body 12 at the manufacturer's facility can be set at a value as high as about 60 pounds or even more in order to prevent accidental separation of the components during normal use. Such installation force should exceed the forces likely to be encountered during normal use. Rotation of barbed tube 26 can be easily performed despite the significant snap-in force between the components.

Another significant benefit of this preferred construction is that a fluid-tight seal is created and maintained between the components. The O-ring seal created by O-ring 40 prevents the passage of liquid or gaseous fluid between the components. This radial O-ring seal is maintained even as barrel 28 and barbed tube 26 are rotated with respect to the probe's body so that such rotation can be performed during use of the probe without causing leakage, even as fluid is flowing through the probe.

Yet another significant benefit of this preferred construction, as suggested before, is that the barbed tube 26 can be rotated with respect to the probe body 12 in order to adjust the position of barb 30 with respect to the axis of the probe body. Such rotation can be made without causing axial displacement of one of the components with respect to the other. In other words, the embodiment described in FIGS. 3 and 4 permits rotation of barbed tube 26 with respect to probe body 12 without causing upward or downward movement of barbed tube 26 with respect to probe body 12 along the axis of barrel 28. Such a connection is preferred to a threaded engagement, for example, because a threaded connection can be loosened upon rotation of the components with respect to one another.

The operation of preferred probe 10 will now be described with reference to the figures. Probe 10 is adapted to be held in the hand of a surgeon or other technician. It is adapted to provide a controlled introduction of fluid into an operative site. It is also adapted to permit the controlled suction of fluid from the operative site.

Depression of finger rest 60 on irrigation valve 22 permits the flow of liquid or gaseous fluid from a fluid source (not shown), through the valve 22, into the probe body 12, through the probe shaft 14 and into the operative site. Irrigation valve 22 is most frequently used in an "on" or "off" condition when it is alternatively fully depressed or fully released to its rest position, respectively. Irrigation valve 22 is optionally used in a partially opened position by partially depressing the finger rest, thereby providing a passageway, albeit reduced, for fluid flow.

Suction valve 24 operates in a similar manner to irrigation valve 22, except that it provides controlled suction of fluid from the operative site. A finger rest on suction valve 24 is fully depressed in order to cause maximum suction of liquid or gaseous fluid, tissue or other solid debris from an operative site through probe shaft 14, through probe body 12, and out through flexible hose 31 to a suction source (not shown). It will be understood that suction valve 24, when opened, provides a large passage with a minimum number of turns so that materials can be removed easily. In order to perform a partial suction or aspiration of an operative site, such as when smoke is to be evacuated after a cauterization procedure, an optional smoke evacuation feature can be utilized to partially and controllably open suction valve 24. If a smoke evacuation feature requires rotation of the finger rest or any other component of the suction valve to permit partial suction, then the torque required for smoke evacuation is preferably less than the torque required to rotate the suction valve's barrel with respect to probe body 12. Accordingly, a surgeon can adjust such a smoke evacuation feature without causing rotation of flexible hose 31 about the axis of the suction valve's barrel.

Many modifications to the preferred embodiments shown and described can be made without departing from the spirit and scope of this invention. For example, the probe can be formed in a variety of shapes and sizes and the components of the probe can be provided with a wide variety of configurations and can be formed from a wide variety of materials. Also, although the preferred embodiment includes a valve for suction and a separate valve for irrigation, a probe according to this invention can have a single valve for suction or for irrigation. It is also contemplated that a single valve can be used either for suction or for irrigation depending on the manner in which the probe is connected to the sources of irrigation fluid and suction.

It is also contemplated that the configuration of the valve or valves with respect to the probe's body can be modified significantly depending on design preferences. For example, the barbed tube portion of the valve can be positioned below the probe body or on the opposite side of the probe body from the finger rest. Referring to FIG. 3 as a point of reference, barbed tube 26 can be positioned below probe body 12 and the top or side of barbed tube 26 can be open to the interior passageway of probe body 12. In such an embodiment, a portion of the barrel can be positioned above the probe body and a portion below, and the bottom of the barrel can be closed. Also, the axis of such a barrel can either intersect with the axis of the passageway of the probe body or not, depending on design preferences. In other words, the axis of the barrel is optionally offset from the axis of the probe body. Again referring to FIG. 3, the barrel can be positioned to the side of probe body 12 so that the barrel axis is offset from the body axis. In such an embodiment, recesses 48 and 50 on piston 42 are aligned with an opening in the side of the body in a closed valve position and transverse hole 46 is aligned with the side opening of the body in an open valve position. In any event, the barbed tube component is rotatable with respect to the probe body so that the relative position of the supply or discharge opening (such as barb 30) can be adjusted according to user preference.

Figure 5:
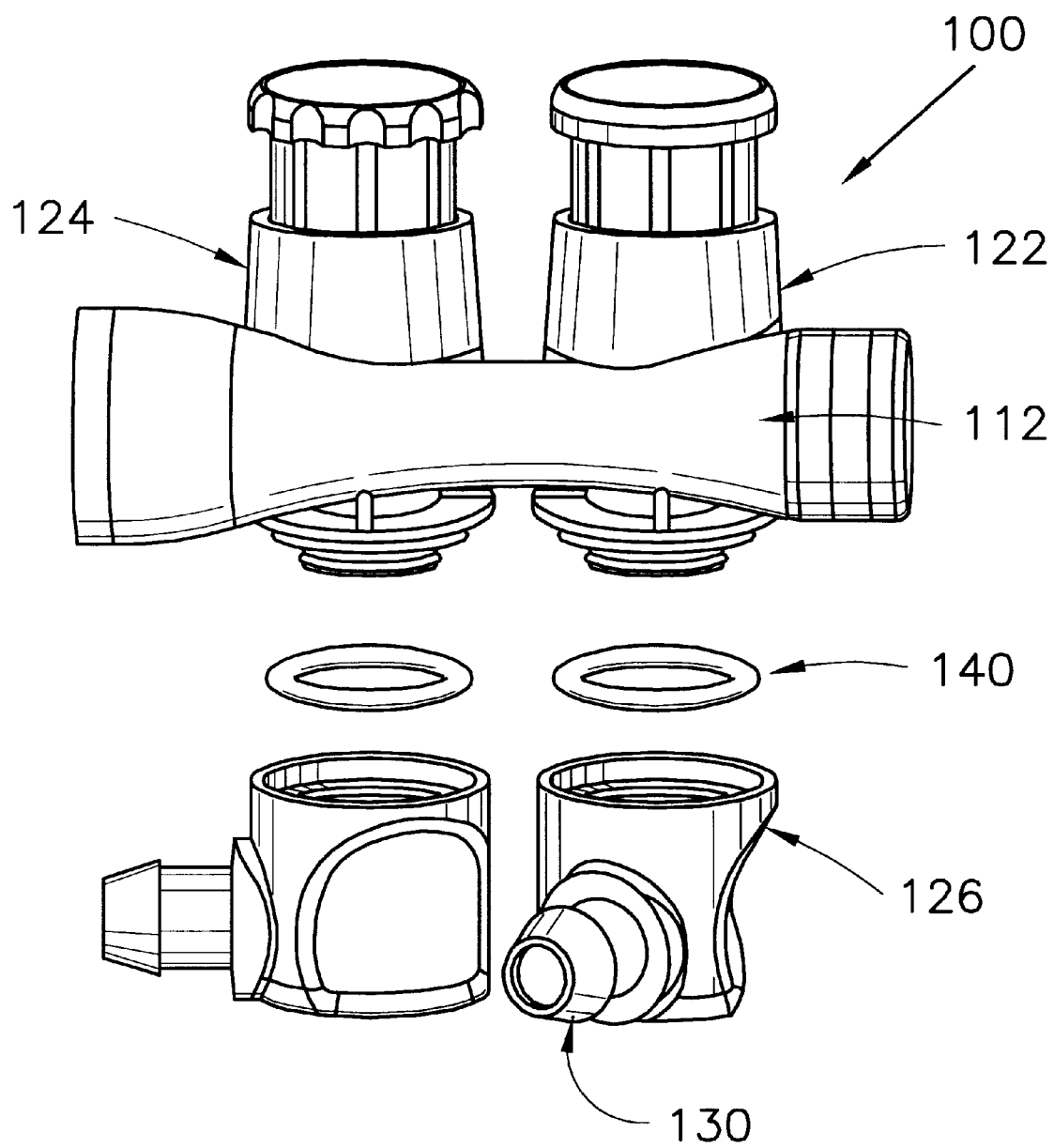
FIG. 5 shows an exploded perspective view of another embodiment of a suction and irrigation probe according to this invention.

For example, an alternative embodiment is illustrated in FIG. 5, wherein a probe generally designated by the numeral "100" is shown in an exploded perspective view. Probe 100 includes an irrigation valve 122 and a suction valve 124 which operate in essentially the same manner as irrigation valve 22 and suction valve 24. The valves 122 and 124 are connected to a probe body portion 112. Referring specifically to aspects of irrigation valve 122, a barbed tube 126 is mounted to a lower portion of probe body 112. Barbed tube 126 defines a portion of the valve's barrel and includes a barb 130 to permit flow into or out from the barrel through a hose (not shown). Barbed tube 126, in this embodiment, has a capped bottom end. A snap-in engagement is preferably provided between barbed tube 126 and probe body 112 to hold the components together while permitting their relative rotation. Also, an O-ring 140 is provided between barbed tube 126 and probe body 112 to form a face or radial seal between those components, while permitting rotation.

Also, although a preferred embodiment of the connection between the probe body and the valve is illustrated in FIGS. 3 and 4, a wide variety of connections are contemplated. For example, the O-ring seal of the illustrated embodiment is optionally replaced with one or more alternative seals or seal cross-sections. Also, the radial O-ring seal illustrated is optionally replaced with a face seal, perhaps between facing surfaces of the barrel and the probe body, for example.

Furthermore, alternative structures for engaging the barrel to the probe are contemplated as well. Although snap-in or interference fit engagements may be preferred, equivalent means for retaining the barrel are contemplated.

In any embodiment, a probe according to this invention will have significant benefits. For example, the probe can be easily adjusted for use in the right or left hand to comfortably accommodate a wide variety of users. It can also be adjusted during a surgical procedure to accommodate the needs or styles of multiple users or to permit a single operator to alternate hands. Also, a probe according to this invention is preferably adjustable "on the fly" while it is being used to irrigate or evacuate an operative site.

While many modifications to the preferred embodiment have been described, it is contemplated that additional modifications can be made without departing from the spirit or scope of the invention, which is defined separately in the claims that follow.

What is claimed is:

1. A hand-held surgical device for controlled flow into or out from a surgical patient, wherein said device is adapted for adjustment for use in a right or left hand, said device comprising:

a body defining a flow passageway;

a valve connected to said body adapted to control flow into or suction out of said flow passageway defined by said body, said valve comprising a barrel positioned for flow communication with said flow passageway defined by said body and a port defined by said barrel and positioned for flow into or out from said valve;

wherein said barrel is mounted to said body for rotation about an axis of said barrel, and wherein said rotation of said barrel changes the orientation of said port with respect to said body to permit adjustment of said orientation on the fly during surgical use of said device.

2. The device defined in claim 1, wherein said valve comprises an irrigation valve connected to said body for controlled flow of irrigation fluid toward said flow passageway defined by said body.

3. The device defined in claim 1, wherein said valve comprises a suction valve connected to said body for controlled suction from said flow passage defined by said body.

4. The device defined in claim 3, wherein said suction valve is adjustable to permit a reduced level of suction by applying torque for rotating a component of said valve with respect to said barrel.

5. The device defined in claim 4, wherein the torque required to rotate said component with respect to said barrel is less than the torque required to rotate said barrel with respect to said body.

6. The device defined in claim 1, wherein said port is oriented for flow along an axis substantially perpendicular to said axis of said barrel.

7. The device defined in claim 1, wherein said barrel is rotated with respect to said body while maintaining a substantially constant position of said barrel with respect to said body in the direction along said axis of said barrel.

8. The device defined in claim 1, wherein said barrel comprises a mounting portion lockingly and sealingly engaged adjacent to an opening defined in said body.

9. The device defined in claim 8, wherein a groove is defined on said mounting portion or adjacent to said opening defined in said body for locking engagement with a bead defined adjacent to said opening or on said mounting portion, respectively, to lockingly engage said mounting portion adjacent to said opening while permitting said rotation of said barrel with respect to said body.

10. The device defined in claim 8, wherein said device further comprises an elastomeric seal mounted in a groove defined between said mounting portion and said body, said elastomeric seal being positioned to form a seal between said mounting portion and said body while permitting said rotation of said barrel with respect to said body.

11. The device defined in claim 1, wherein said barrel is mounted to said body with sufficient force to prevent the separation of said barrel from said body during normal use of said device while permitting said rotation of said barrel with respect to said body.

12. A probe for controlling flow into or out from an operative site, wherein said probe is adjustable for use in a right or left hand or for alternating use between a right and left hand during use of said probe, said probe comprising:

a body defining a passageway for flow toward or away from said operative site;

a piston valve connected to said body adapted to control flow into or suction out of said passageway defined by said body, said piston valve comprising a barrel positioned for flow communication with said passageway defined by said body and a port defined by said barrel and positioned for flow into or out from said piston valve; and means for lockingly and sealingly engaging said barrel of said piston valve to said body and for rotating said barrel with respect to said body about an axis of said barrel, wherein rotation of said barrel with respect to said body adjusts the orientation of said port with respect to said body during use of said probe.

13. The probe defined in claim 12, wherein said means comprises a groove defined on said barrel or on said body for locking engagement with a bead defined on said body or on said barrel, respectively, to lockingly engage said barrel to said body while permitting said rotation of said barrel with respect to said body.

14. The probe defined in claim 12, wherein said means comprises an elastomeric seal mounted between said barrel and said body, said elastomeric seal being positioned to form a seal between said barrel and said body while permitting said rotation of said barrel with respect to said body.

15. A hand-held device for introducing fluid into an operative site for irrigation or for suction of fluid from said operative site, wherein said device is adjustable for use in a right or left hand of a user or for alternating use between a right and left hand of a user during operation of said device, as desired, said device comprising:

a body portion adapted to be grasped in a hand, said body portion defining a passageway for fluid flow toward or away from said operative site;

a piston valve connected to said body portion adapted to control fluid flow into or suction out of said passageway defined by said body portion, said valve comprising a barrel and a port defined in a wall of said barrel to permit fluid flow into or out from said piston valve;

said barrel being mounted to said body portion for fluid flow communication between said barrel and said passageway and for rotation of said barrel with respect to said body portion about a barrel axis;

wherein said rotation of said barrel with respect to said body portion changes the orientation of said port with respect to said body portion and adjusts said orientation of said port for use of said device in a right or left hand or for alternating use between right and left hands, wherein said adjustment can be made during use of said device for introducing fluid or for suction of fluid, and wherein said barrel is lockingly engaged to said body portion with sufficient force to prevent separation of said barrel from said body portion during normal use of said device while permitting said rotation of said barrel with respect to said body portion.

16. The device defined in claim 15, wherein said device comprises an irrigation valve connected to said body portion to permit controlled fluid flow toward said passageway and a suction valve connected to said body portion to permit controlled fluid flow out from said passageway.

17. The device defined in claim 16, wherein said irrigation valve and said suction valve each comprises a barrel mounted for rotation with respect to said body portion.

18. The device defined in claim 16, wherein said suction valve is adjustable to permit a reduced level of suction of a liquid from said operative site and evacuation of a gas from said operative site.

19. The device defined in claim 18, wherein said suction valve comprises a member mounted for rotation under the influence of torque with respect to said barrel to permit controlled suction of said gas from said operative site as needed by the user of said device, wherein the torque required to rotate said member with respect to said barrel is less than the torque required to rotate said barrel with respect to said body portion.

20. The device defined in claim 15, wherein a radial groove is defined on an outer surface of said barrel or on an inner surface of an opening defined in said body portion for locking engagement with a radial bead defined on said inner surface of said opening or on said outer surface of said barrel, respectively, to lockingly engage said barrel portion adjacent to said opening while permitting said rotation of said barrel with respect to said body portion.

21. The device defined in claim 15, wherein said device further comprises an elastomeric seal mounted in a radial groove defined between an outer surface of said barrel and an inner surface of an opening defined by said body portion, said elastomeric seal being positioned to form a seal between said barrel and said body portion while permitting said rotation of said barrel with respect to said body portion.

* * * * *